United States Patent [19]

Ferrand et al.

[11] Patent Number: 4,957,927
[45] Date of Patent: Sep. 18, 1990

[54] (DIARYLMETHOXY ALKYL)-1-PYRROLIDINES AND-PIPERIDINES HAVING CARDIOVASCULAR ACTIVITY

[75] Inventors: Gerard Ferrand, Lyons; Jacques Barbanton, Brignais; Jean-Claude Depin, Lyons; Gilles Chavernac, La Mulatiere, all of France

[73] Assignee: Lipha, Lyonnaise Industrielle Pharmaceutique, Lyons, France

[21] Appl. No.: 410,705

[22] Filed: Sep. 22, 1989

[30] Foreign Application Priority Data

Sep. 23, 1988 [FR] France ............................... 88 12430

[51] Int. Cl.$^5$ ................ C07D 207/04; C07D 211/04; A61K 31/445; A61K 31/40
[52] U.S. Cl. .................................. 514/428; 514/317; 546/236; 548/574
[58] Field of Search ........................ 546/236; 548/574; 514/317, 428

[56] References Cited

U.S. PATENT DOCUMENTS 4,202,896 5/1980 Gouttes ............................... 544/397

OTHER PUBLICATIONS

March, Advanced Organic Chemistry, 2nd Ed., pp. 382 and 1122, McGraw-Hill Pub., 1979.
Chemical Abstracts, vol. 101, 1984, p. 37, No. 65725p,
E. Lardner et al.: "Hoe 263, a new substance with calcium channel antagonistic activity".

Primary Examiner—Alan L. Rotman
Assistant Examiner—Joseph K. McKane
Attorney, Agent, or Firm—Browdy and Neimark

[57] ABSTRACT

1-[(diarylmethoxy)alkyl]pyrrolidines and piperidines represented by the following formula:

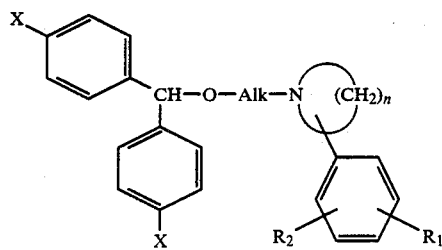

wherein X is hydrogen or a fluorine atom, Alk is a linear-chain or branched alkyl group having two or three carbon atoms; $R_1$ and $R_2$ are hydrogen or a linear-chain or branched alkoxy radical having 1 to 4 carbon atoms; n is 4 or 5.

The compounds can be used as cardiovascular medicines.

7 Claims, No Drawings

(DIARYLMETHOXY ALKYL)-1-PYRROLIDINES AND-PIPERIDINES HAVING CARDIOVASCULAR ACTIVITY

FIELD OF THE INVENTION

This invention relates to new 1-[(diarylmethoxy)alkyl]-pyrrolidines and piperidines according to general formula I.

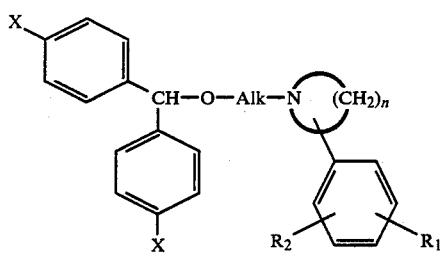

wherein X is hydrogen or a fluorine atom; Alk is a linear-chain or branched alkyl group containing 2 or 3 carbon atoms; $R_1$ and $R_2$ are hydrogen or a linear-chain or branched alkoxy radical having 1 to 4 carbon atoms and able to occupy any position on the aromatic core; n may be 4 or 5.

Compounds having formula I wherein Alk is a linear-chain alkyl group constitute an especially interesting class of compounds.

SUMMARY OF THE INVENTION

The pharmaceutically-acceptable salts are an integral part of the invention. They can be salts prepared using mineral acids such as hydrochloric acid, hydrobromic acid, sulfuric acid, phosphoric acid, or using organic acids such as tartaric acid, citric acid, acetic acid, maleic acid, fumaric acid, oxalic acid, methanesulfonic acid.

The products according to the invention can be prepared using the following sequence of reactions, wherein X, $R_1$, $R_2$ and n have the meanings indicated above.

A bromodiphenylmethane having formula II is condensed with a bromoalkanol having the general formula III. The reaction can take place in the presence of an alkaline agent in an inert solvent, or in the absence of a solvent. Good results have been obtained by working in the presence of a carbonate of an alkaline metal such as sodium or potassium, at a temperature of 80° to 150° C. We obtain the compounds according to the invention by condensing the resulting halogenide having general formula IV with an arylpyrrolidine or an arylpiperidine having general formula V. The latter reaction takes place advantageously in an inert solvent in the presence of a base. Preferred bases are carbonates and hydrides of alkaline metals such as sodium and potassium. The reaction temperature can be between room temperature and the boiling point of the solvent used.

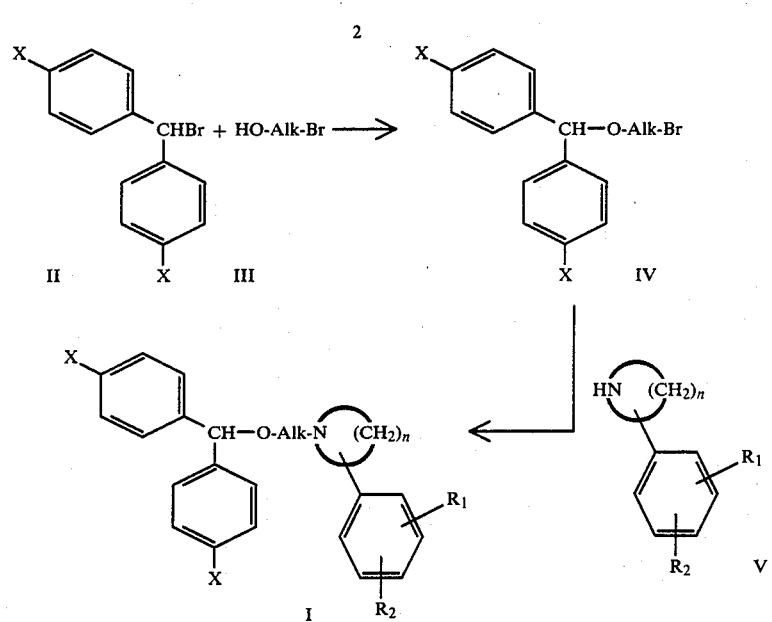

The products according to the invention, wherein X is hydrogen and Alk is the ethylene radical —CH$_2$—CH$_2$—, can also be obtained using the following reactive sequence, wherein $R_1$, and $R_2$ and n have the meanings given above:

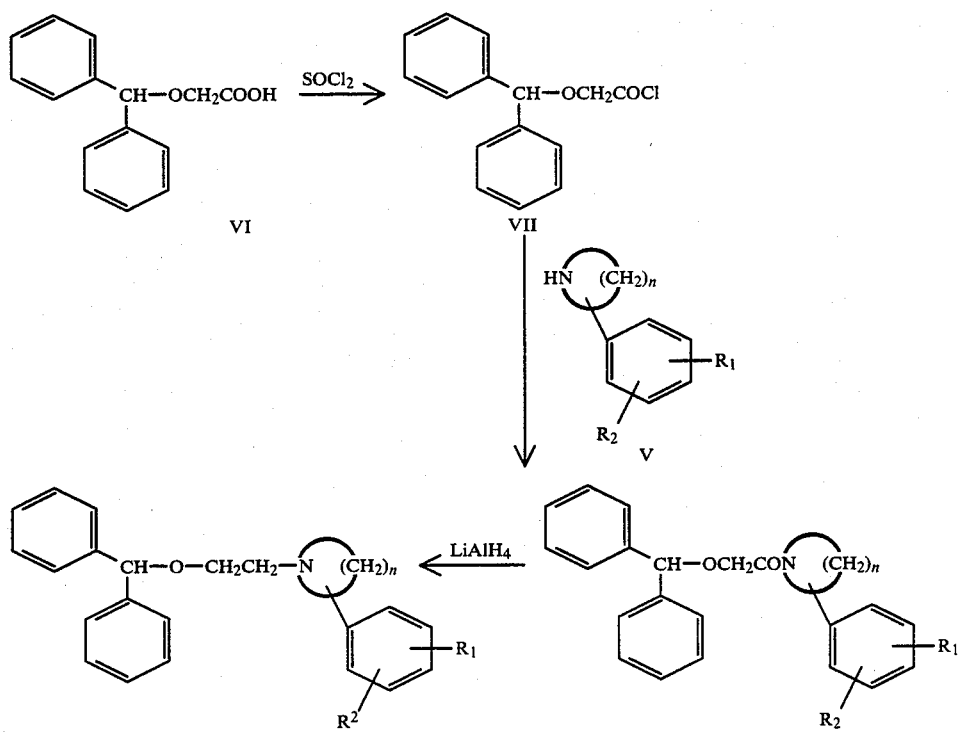

Diphenylmethoxy acetic acid VI treated with thionyl chloride supplies the chloride VII that is condensed with an arylpiperidine or an arylpyrrolidine having general formula V. The amides VIII obtained are then reduced using lithium aluminum hydride. We generally proceed with an excess of reducing agent in an ethereal solvent such as diethyl ether or tetrahydrofuran.

We have noted that the compounds represented by Formula I have remarkable calcium-antagonistic properties that make them useful in human medicine, especially in treating cerebral and peripheral vascular diseases, vestibular disorders and the prevention of migraines.

The calcium-inhibitive effect was researched in vitro using the method described by J. M. Van Neuten (Eur. J. Pharmacol., 1969, 6, 286) on the isolated depolarized artery of the rabbit's ear:

A fragment of the central artery of the ear was cannulated and suspended in 100 ml of a Tyrode solution [NaCl: 136.90 mmole/l; KCl: 2.68 mmole/l; CaCl$_2$: 3.60 mmole/l; MgCl$_2$: 1.04 mmole/l; NaH$_2$PO$_4$: 0.42 mmole/l; glucose: 5.55 mmole/l, NaHCO$_3$: 11.90 mmole/l ]. The fragment was oxygenated (O$_2$: 95%; CO$_2$: 5%) and perfused with a constant 2-ml/minute flow of Tyrode at 37° C. Pressure changes in the perfusion circuit were recorded continuously using a pressure sensor. After an equilibration period, the Tyrode was replaced with a hyperpotassic depolarizing solution [NaCl: 39.33 mmole/l; KCl: 99.83 mmole/l; CaCl$_2$: 3.60 mmole/l; MgCl$_2$: 1.04 mmole/l; NaH$_2$PO$_4$: 0.42 mmole/l; glucose: 5.55 mmole/l; NaHCO$_3$: 11.90 mmole/l ], which, because of intracellular calcium penetration, caused significant and durable vasoconstriction, antagonized by a calcium inhibitor. The products according to the invention were tested in a single dose of 10 μg administered by injection into the perfusion system, at a rate of 0.1 ml for 10 seconds. This is the dose that produces a lasting decrease in pressure of about 50% upon the injection of flunarizine used as a standard. The effects of the products according to the invention on vasoconstriction induced by the hyperpotassic solution were monitored for several hours. The intensity was measured at the peak of their action.

Each product was tested on at least three artery fragments. Table I includes the average decreases in perfusion pressure observed for a few products according to the invention.

The calcium-antagonistic effect of the products according to the invention is substantially intracellular. This was demonstrated by studying their action on a calcium-transporting protein, calmodulin. The principle of the method used is the activating effect calmodulin has on the basic enzyme activity of Type I cardiac phosphodiesterase (H. C. Ho et al., Biochim. Biophys. Acta 1976, 429, 461). Enzyme activity is measured using the W. J. Thomson and H. M. Appleman technique (Biochemistry, 1971, 10, 311). In this test, the products according to the invention show significant anti-calmodulin activity. Thus, the product described in example 10 has an inhibitive concentration 50 of 83 μM, while the inhibition obtained with flunarizine is only 6% at 100 μM under the same conditions.

TABLE 1

| PRODUCTS | % DROP IN PERFUSION PRESSURE ± STANDARD ERROR |
|---|---|
| EXAMPLE 1 | 56 ± 6 |
| EXAMPLE 4 | 54 ± 5 |
| EXAMPLE 10 | 59 ± 4 |
| EXAMPLE 11 | 56 ± 5 |
| EXAMPLE 13 | 58 ± 5 |
| EXAMPLE 14 | 54 ± 5 |
| EXAMPLE 15 | 52 ± 5 |
| FLUNARIZINE | 41 ± 4 |

The compounds according to this invention exhibit a very slight toxicity. Thus, the compound in example 10 has a lethal dose 50 in rats greater than 1 g/kg when administered orally.

This application also has as an object the implementation of compounds I as medicines, especially cardiovascular medicines. These medicines can be administered orally in the form of tablets, coated tables or capsules, or intravenously in injectable aqueous solution form. The main active ingredient is combined with various pharmaceutically-compatible excipients. Daily posologies can vary from 1 mg to 100 mg of active agent, depending on the patient's age and the seriousness of the condition treated.

Below are a few pharmaceutical formulas, provided as non-restrictive examples:

| Composition of a 100 mg tablet, coated or otherwise: | |
|---|---|
| Active agent | 10 mg |
| Lactose | 40 mg |
| Wheat starch | 37 mg |
| Gelatin | 2 mg |
| Alginic acid | 5 mg |
| Talc | 5 mg |
| Magnesium stearate | 1 mg |
| Composition of a capsule: | |
| Active agent | 10 mg |
| Lactose | 32 mg |
| Wheat starch | 25 mg |
| Talc | 2.5 mg |
| Magnesium stearate | 0.5 mg |

DETAILED DESCRIPTION OF THE INVENTION

The following examples illustrate the invention on a non-restrictive basis.

EXAMPLE I

1-[2-diphenylmethoxy)ethyl]-3-(3-methoxyphenyl) pyrrolidine oxalate (a) 1-(diphenylmethoxy)-2-bromoethane 37.5 g (0.3 mole) of 2-bromoethanol was added to a mixture of 61.8 g (0.25 mole) of bromodiphenylmethane and 31.8 g (0.3 mole) of sodium carbonate. The reactive medium was slowly heated to 130° C., held at this temperature for 5 hours and then left overnight at room temperature. The mixture was taken up with ether and washed with water. The ethereal extract was dried on sodium sulfate. The evaporation of the ether yielded an oil, which was purified by distillation.
Yield: 55 g (75%).
Boiling Point$_{0.25-0.3}$=128°-135° C.

(b) 1-[2-(diphenylmethoxy)ethyl]-3-(3-methoxyphenyl)pyrrolidine oxalate

A solution of 17.5 g (60 mmole) of 1-(diphenylmethoxy)-2-bromoethane in 50 cm$^3$ of dimethylformamide was added to a mixture of 10.6 g (60 mmole) of 3-(3-methoxyphenyl)pyrrolidine [prepared according to A. Ebnother and K. Hasspacher, Swiss Patent No. 526 536], 16.6 g (120 mmole) of potassium carbonate, 300 cm$^3$ of dimethylformamide and a few potassium iodide crystals. The mixture was heated at 80° C. for 13 hours, and concentrated to dryness under reduced pressure after it returned to room temperature. The residue was taken up with 500 cm$^3$ of 1N hydrochloric acid and extracted with ether. The aqueous acid phase was separated, basified with 10N sodium hydroxide solution, and extracted with methylene chloride. The organic solution was dried on sodium sulfate. The evaporation of the solvent provided an oily residue. Purification by silica gel filtration (eluent, hexane-ethyl acetate, 1/1) yielded 10 g of 1-[2-(diphenylmethoxy) ethyl]-3-(3-methoxyphenyl)pyrrolidine, which was dissolved in 100 cm$^3$ of ether. To this solution was added a solution of 2.55 g (28.3 mmole) of oxalic acid in 30 cm$^3$ of acetone. The oxalate precipitate was filtered and recrystallized from acetone.
Yield: 9.0 g (31%).
F=133°-134° C.
Elemental analysis: $C_{28}H_{31}NO_6$ (M=477.56)

|  | C % | H % | N % |
|---|---|---|---|
| Calculated | 70.42 | 6.54 | 2.93 |
| Obtained | 70.53 | 6.71 | 2.87 |

NMR (DMSO d6): δ=3.0-3.9 [with peak at 3.7] (multiplet, 14H) 5.5 (singlet, 1H); 6.6 (enlarged peak, 2H, can be exchanged with CF$_3$COOD); 6.7-7.6 (multiplet, 14H).

EXAMPLE 2

1-[2-(diphenylmethoxy)ethyl]-3-(3-methoxyphenyl) pyrrolidine chlorohydrate 1.35 cm$^3$ of a 7.4M solution of hydrogen chloride gas in ethanol was added to a solution of 3.9 g of 1-[2-(diphenylmethoxy) ethyl]-3-(3-methoxyphenyl)pyrrolidine [prepared according to Example 1 above] in 100 cm$^3$ of ether. The precipitate was filtered and recrystallized from acetone.
Yield: 1.8 g (42%)
F=118°-120° C.
Elemental analysis: $C_{26}H_{30}ClNO_2$ (M=423.98)

|  | C % | H % | Cl % | N % |
|---|---|---|---|---|
| Calculated | 73.66 | 7.13 | 8.36 | 3.30 |
| Obtained | 73.36 | 7.10 | 8.44 | 3.32 |

EXAMPLE 3

1-[2-(diphenylmethoxy)ethyl-4-(3-methoxyphenyl piperidine oxalate

Proceeding as in Example 1, using 5.8 g (20 mmole) of 1-(diphenylmethoxy)-2-bromoethane, 3.8 g (20 mmole) of 4-(3-methoxyphenyl)piperidine [prepared using the B. M. Iselin and K. Hoffmann method, Helv. Chim. Acta 1954, 37 178] and 5.5 g (40 mmole) of potassium carbonate, there was obtained after silica gel column filtration and oxalic acid solidification, 4.9 g (yield: 50%) of the desired product.
F=145°-146° C. (acetone-ethanol).
Elemental analysis: $C_{29}H_{33}NO_6$ (M=491.58)

|  | C % | H % | N % |
|---|---|---|---|
| Calculated | 70.86 | 6.77 | 2.85 |
| Obtained | 70.66 | 6.76 | 2.73 |

EXAMPLE 4

3-(3,4dimethoxyphenyl)-1-[2-diphenylmethoxy)ethyl]-pyrrolidine oxalate

Proceeding as in Example 1, using 14.5 g (49.7 mmole) of 1-(diphenylmethoxy)2-bromoethane, 10.3 g (49.7 mmole) of 3-(3,4-dimethoxyphenyl)pyrrolidine [prepared using the A. Ebnother and K. Hasspacher method, Swiss Patent No. 526 536] and 13.8 g (100 mmole) of potassium carbonate, there was obtained after silica gel column filtration (eluent, hexane-ethyl acetate, 1/1) 10.1 g (yield: 49%) of 3-(3,4 dimethoxyphenyl)-1-[2-(diphenylmethoxy)ethyl]pyrrolidine oxalate, in the form of a thick oil.

A solution of 8.5 g (20.3 mmole) of base in 40 cm$^3$ of acetone, was treated with a solution of 1.8 g of oxalic acid in 10 cm$^3$ of acetone. The oxalate precipitate was filtered and recrystallized from ethanol. There was obtained 7.8 g (overall yield: 37%) of 3-(3,4 dimethoxyphenyl)-1-[2-(diphenylmethoxy) ethyl]pyrrolidine oxalate.

F=165°-167° C.

Elemental analysis: $C_{29}H_{33}NO_7$ (M=507.58)

|  | C % | H % | N % |
|---|---|---|---|
| Calculated | 68.62 | 6.55 | 2.76 |
| Obtained | 68.36 | 6.38 | 2.79 |

EXAMPLE 5

1-[2-(diphenylmethoxy)ethyl-3-phenylpyrrolidine chlorohydrate

Proceeding as in Example 1, using 14.6 g (50 mmole) of 1-(diphenylmethoxy)-2-bromoethane, 7.3 g (50 mmole) of 3-phenyl pyrrolidine and 13.8 g (100 mmole) of potassium carbonate, there was obtained after silica gel column filtration (eluent, hexaneethyl acetate, 1/1), 11 g (yield: 61.5%) of 1-[2-(diphenyl methoxy)ethyl-3-phenylpyrrolidine in the form of a thick oil.

A solution of 9 g (25.2 mmole) of base in 150 cm$^3$ of ether, was treated with 3.7 cm$^3$ of a 7.4M solution of hydrogen chloride gas in ethanol. The chlorhydrate precipitate was filtered and recrystallized from acetone. There was obtained 5.7 g (overall yield: 35%) of 1-[2-(diphenylmethoxy)ethyl-3-phenyl pyrrolidine chlorohydrate.

F=131°-132° C.

Elemental analysis: $C_{25}H_{28}ClNO$ (M=393.96)

|  | C % | H % | Cl % | N % |
|---|---|---|---|---|
| Calculated | 76.22 | 7.16 | 9.00 | 3.56 |
| Obtained | 76.03 | 7.19 | 9.05 | 3.62 |

EXAMPLE 6

1-[3-(diphenylmethoxy)propyl]-3-(3-methoxyphenyl) pyrrolidine chlorohydrate

(a) 1-(diphenylmethoxy)-3-bromopropane

A mixture of 12.3 g (50 mmole) of bromodiphenylmethane, 8.3 g (60 mmole) of 3-bromopropanol and 6.3 g (60 mmole) of sodium carbonate was heated at 120°-130° C. for 10 hours and then left overnight at room temperature. The mixture was extracted with ether and washed with water. The ethereal extract was dried on sodium sulfate. Evaporation of the ether yielded an oil, which was purified by distillation.

Yield: 9.1 g (60%)

Boiling Point$_{0.25}$=130°-140° C.

(b) 1-[3-(diphenylmethoxy)propyl]-3-(3-methoxyphenyl)-pyrrolidine chlorohydrate A solution of 5.3 g (50 mmole) of 1-(diphenylmethoxy)-3-bromopropane in 50 cm$^3$ of dimethylformamide was added to a mixture of 8.8 g (50 mmole) of 3-(3-methoxyphenyl)pyrrolidine, 13.8 g (100 mmole) of potassium carbonate, a few potassium iodide crystals and 250 cm$^3$ of dimethylformamide. The reactive medium was heated to 80° C. for 12 hours and then filtered after it returned to room temperature. The filtrate was concentrated to dryness under reduced pressure. The residue was taken up with ether and extracted with 500 cm$^3$ of N hydrochloric acid. The aqueous phase was separated, basified with 10N sodium hydroxide solution and extracted with methylene chloride. The organic solution was dried on sodium sulfate. Evaporation of the solvent yielded an oily residue, which was purified by silica gel column filtration (eluent, hexane-ethyl acetate, 1/1). There was obtained 10.3 g (yield: 51.3%) of 1-[3-(diphenylmethoxy)propyl] 3-(3-methoxyphenyl)pyrrolidine.

A 7.4M solution of hydrogen chloride gas in ethanol was added to a solution of 9 g of base in 150 cm$^3$ of ether. The precipitate was filtered and recrystallized from ethyl acetate. There was obtained 7.4 g (overall yield: 39%) of 1-[3-(diphenyl methoxy)propyl]-3-(3-methoxyphenyl)pyrrolidine chlorohydrate.

F=109°-110° C.

Elemental analysis: $C_{27}H_{32}ClNO_2$ (M=438.01)

|  | C % | H % | Cl % | N % |
|---|---|---|---|---|
| Calculated | 74.04 | 7.36 | 8.09 | 3.20 |
| Obtained | 73.85 | 7.43 | 8.14 | 2.96 |

NMR (CDCl$_3$): $\delta$=2.0-2.7 (multiplet, 4H); 2.9-4.2 (multiplet, 12H); 5.3 (singlet, 1H); 6.6-7.5 (multiplet, 14H).

EXAMPLE 7

1-[3-(diphenylmethoxy)-2-propyl]-3-(3-methoxyphenyl)

(a) 1-(diphenylmethoxy)-2-bromopropane

A mixture of 12.4 g (50 mmole) of bromodiphenylmethane, 6.4 g (60 mmole) of sodium carbonate and 8.3 g (60 mmole) of 2-bromopropanol [prepared according to R. F. Nystrom, J. Am. Chem. Soc. 1959, 81, 610] was heated to 130° C. in 2 hours, and was held at this temperature for 8 hours. After the reactive medium returned to room temperature, it was diluted with ether and washed with water. The ethereal phase was separated, and the solvent was then evaporated. Distillation of the residue yielded the 1-(diphenylmethoxy)-2-bromopane used subsequently, with no further purification.

Yield: 10.5 g (69%)

Boiling point$_{0.4}$=120°-130° C.

(b)
1-[3-(diphenylmethoxy)-2-propyl]-3-(3-methoxy-phenyl)pyrrolidone oxalate

A solution of 10.5 g (34.4 mmole) of 1-(diphenyl methoxy)-2-bromopropane in 50 cm³ of dimethylformamide was added quickly to a mixture of 6.1 g (34.4 mmole) of (methoxy-3 phenyl)-3 pyrrolidine, 9.5 g (68.8 mmole) of potassium carbonate, 150 cm³ of dimethylformamide and a few iodine crystals. The reaction medium was stirred for 14 hours at 60° C. The insoluble mineral materials were filtered, and the solution was then concentrated to dryness under reduced pressure. The residue was taken up with 5N hydrochloric acid and washed with ether. The aqueous phase was separated and basified with 5N sodium hydroxide solution. The mixture was extracted with methylene chloride. The organic solution was washed with water, dried on sodium sulfate and concentrated dry. The oily residue was silica gel column filtered (eluent, hexane-ethyl acetate, 1/1). There was obtained 3.9 g of an oil, which was dissolved in 100 cm³ of ether. This solution was treated with a solution of 0.96 g (10.6 mmole) of oxalic acid in 20 cm³ of acetone. The 1-[3-(diphenylmethoxy)-2-propyl]-3-(3-methoxyphenyl)pyrrolidine oxalate was filtered and recrystallized from acetone.

Yield: 2.2 g (11%)
F=119°–121° C.
Elemental analysis: $C_{29}H_{33}NO_6$ (M=491.58)

|  | C % | H % | N % |
|---|---|---|---|
| Calculated | 70.86 | 6.77 | 2.85 |
| Obtained | 70.80 | 6.57 | 3.00 |

NMR (CDCl₃): $\delta$=1.4 (doublet, 2H); 2.0–2.7 (multiplet, 2H); 2.9–4.2 (multiplet, 10H, 2 of which can be exchanged by CF₃COOD); 5.3 (singlet, 1H); 6.6–7.7 (multiplet, 14H).

EXAMPLE 8

1-[2-(diphenylmethoxy)ethyl]-2-phenylpyrrolidine oxalate

Proceeding as in Example 1, using 14.6 g (50 mmole) of 1-diphenylmethoxy)-2-bromoethane, 7.3 g (50 mmole) of 2-phenyl pyrrolidine and 13.8 g (100 mmole) of potassium carbonate, there was obtained after silica gel column filtration, 9 g (yield: 50%) of 1-[2-(diphenylmethoxy)ethyl]2-phenylpyrrolidine.

The oxalate was prepared in the traditional manner.
F=90°–94° C. (acetone).
Elemental analysis: $C_{27}H_{29}NO_5$ (M=447.53)

|  | C % | H % | N % |
|---|---|---|---|
| Calculated | 72.46 | 6.53 | 3.13 |
| Obtained | 72.73 | 6.30 | 2.95 |

EXAMPLE 9

1-[2-[bis(4-fluorophenyl)methoxy]ethyl]-3-(3-methoxy-phenylpyrrolidine oxalate (a) 1-[bis(4-fluorophenyl)methoxy]-2-bromoethane A mixture of 49.5 g (0.175 mole) of bromo bis(4-fluoro phenyl)methane, 22.4 g (0.21 mole) of sodium carbonate and 26.9 g (0.21 mole) of 2-bromoethanol was stirred at 130° C. for 15 hours. After cooling, the reaction mixture was taken up with water and extracted with ether. The ethereal phase was washed, dried on sodium sulfate and then concentrated dry. Distillation of the residue yielded 41.9 g (yield: 69.4%) of 1-[bis(4-fluorophenyl) methoxy]-2-bromoethane.

Boiling point$_{0.2}$=119°–123° C.

(b)
1-[2-[bis(4-fluorophenyl)methoxy]ethyl]-3-(3-methoxy-phenyl)pyrrolidine oxalate A solution of 7.2 g (0.022 mole) of 1-[bis(4-fluoro phenyl)methoxy]-2-bromoethane in 20 cm³ of dimethylformamide was added quickly to a mixture of 3.9 g (0.022 mole) of 3-(3-methoxy phenyl)pyrrolidine, 6.1 g (0.044 mole) of potassium carbonate and 110 cm³ of dimethylformamide. The mixture was stirred 16 hours at 80° C., filtered and then concentrated under reduced pressure. The residue was diluted with ether and extracted using a 2N hydrochloric acid solution. The aqueous acid phase was washed with ether, basified with 10N sodium hydroxide solution and extracted with methylene chloride. The organic solution was washed with water, dried on sodium sulfate and concentrated dry providing 9.2 g of a oily residue which was purified using flash silica chromatography (eluent, hexane-ethyl acetate, 1/1). There was obtained 4.5 g (yield: 48%) of 1-[2-[bis(4-fluorophenyl) methoxy]ethyl]-3-(3-methoxy-phenyl)pyrrolidine.

The oxalate salt was prepared by treating a solution of 4.3 g of the base obtained above in 30 cm³ of acetone with a solution of 0.9 g of oxalic acid in 10 cm³ of acetone. The oxalate precipitate was filtered and recrystallized from acetone.

Yield: 3.5 g
F=133°–135° C.
Elemental analysis: $C_{28}H_{29}F_2NO_6$ (M=513.54)

|  | C % | H % | F % | N % |
|---|---|---|---|---|
| Calculated | 65.49 | 5.69 | 7.40 | 2.73 |
| Obtained | 65.37 | 5.73 | 7.30 | 3.01 |

NMR (DMSO d₆): $\delta$=1.7–2.6 ppm (multiplet, 2H): 3.0–4.0 ppm [with peak at 3.7 ppm] (multiplet, 12H); 5.6 ppm (singlet, 1H); 6.7–7.6 ppm (multiplet, 12H); 11.1 ppm (enlarged peak, 2H, can be exchanged with trifluoroacetic acid).

EXAMPLE 10

1-[2-[bis(4-fluorophenyl)methoxy]ethyl]-3-(3-methoxy-phenyl)pyrrolidone fumarate 29.8 g (0.746 mole) of a 60% suspension of sodium hydride in oil was added by portions to a solution of 120.2 g (0.678 mole) of 3-(3-methoxyphenyl)pyrrolidine in 2 l of dimethylformamide. The mixture was heated to 45° C. for 1 hour. A solution of 244.1 g (0.746 mole) of 1-[bis(4-fluorophenyl) methoxy]-2-bromoethane (prepared according to Example 9) in 400 cm³ of dimethylformamide was added, and the mixture was heated to 80° C. for 9 hours. 24.4 g of 1-[bis(4-fluorophenyl)methoxy]-2-bromoethane was added and heating was continued at 80° C. for 4 hours. The reaction medium was concentrated under reduced pressure, diluted with water and extracted with methylene chloride. The organic phase was separated, washed with water and dried on sodium sulfate. Evaporation of the solvent yields an oil that is purified by silica gel column filtration (ethyl acetate eluent). The 1-[2-[bis(4-fluorophenyl)methoxy]ethyl]-3-(3-methoxyphenyl)pyrrolidine produced was dissolved in 500 cm³ of ethanol. A solution of 69.8 g (0.602 mole) of fumaric acid in 150 cm³ of ethanol was added and the mixture was concentrated dry. The residue was triturated in ether, filtered and recrystallized from an ethanol-water mixture to give 216.2 g (yield: 59%) of fumarate.

F = 142°–144° C.

Elemental analysis: $C_{30}H_{31}F_2NO_6$

|  | C % | H % | F % | N % |
|---|---|---|---|---|
| Calculated | 66.78 | 5.79 | 7.04 | 2.60 |
| Obtained | 67.15 | 5.77 | 7.00 | 2.65 |

EXAMPLE 11

1-[2-diphenylmethoxy)ethyl)-2-(3-(methoxyphenyl)pyrrolidine fumarate

Proceeding as in Example 1, using 8.7 g (30 mmole) of 1-(diphenylmethoxy)-2-bromoethane, 5.3 g (30 mmole) of 2-(3-methoxyphenyl)pyrrolidine [prepared according to J. H. Burckhalter and J. H. Short, J. Org. Chem., 1958, 23, 1281]and 8.3 g (60 mmole) of potassium carbonate, there was obtained after silica gel column filtration, 6.2 g (yield: 53%) of 1-[2-(diphenyl methoxy)ethyl]-2-(3-methoxyphenyl)pyrrolidine.

The fumarate was prepared in the traditional manner.

F = 134°–135° C. (acetone-ethanol)

Elemental analysis: $C_{30}H_{33}NO_6$ (M = 503.60)

|  | C % | H % | N % |
|---|---|---|---|
| Calculated | 71.55 | 6.61 | 2.78 |
| Obtained | 71.80 | 6.58 | 2.85 |

EXAMPLE 12

1-[3-[bis(4-fluorophenyl)methoxy]propyl]-3-(3-methoxyphenyl)pyrrolidine fumarate (a) 1-[bis(4-fluorophenyl)methoxy]-3-bromopropane A mixture of 36.9 g (0.130 mole) of bromobis(4-fluorophenyl)methane, 21.7 g (0.156 mole) of 3-bromopropanol, 16.6 g (0.156 mole) of sodium carbonate and a few potassium iodide crystals were heated to 130° C. for 16 hours. After cooling, the reaction mixture was diluted with water and extracted with ether. The ethereal phase was washed with water, dried on sodium sulfate and then concentrated to dryness. Distillation of the residue yielded 30.5 g (yield: 68%) of the desired propane.

Boiling point$_{0.15}$ = 134°–140° C.

(b) 1-[3-[bis(4-fluorophenyl)methoxy]propyl]-3-(3-(methoxyphenyl)pyrrolidine fumarate A solution of 17 g (50 mmole) of 1-[bis(4-fluorophenyl) methoxy]3-bromopropane in 50 cm³ of DMF was added quickly to a mixture of 8.8 g (50 mmole) of 3-(3-methoxyphenyl)pyrrolidine, 13.8 g (100 mmole) of potassium carbonate and 250 cm³ of DMF. The mixture was agitated 10 hours at 80° C., filtered and then concentrated under reduced pressure. The residue was taken up with ether and extracted using an N hydrochloric acid solution. The aqueous acid phase was washed with ether, basified with a 10 N sodium hydroxide solution and extracted with methylene chloride. The organic solution was washed with water, dried on sodium sulfate and concentrated dry, producing 17.4 g of an oil which was purified by flash silica chromatography (eluent, hexane-ethyl acetate, 1/1). There was obtained 12.3 g (yield: 56%) of 1-[3[bis(4-fluorophenyl)methoxy]propyl]-3-(3-methoxyphenyl) pyrrolidine.

The fumarate was prepared using the traditional method.

F = 103°–104° C. (isopropanol)

Elemental analysis: $C_{31}H_{33}F_2NO_6$ (M = 553.60)

|  | C % | H % | F % | N % |
|---|---|---|---|---|
| Calculated | 67.26 | 6.01 | 6.86 | 2.53 |
| Obtained | 67.55 | 6.12 | 6.82 | 2.82 |

EXAMPLE 13

1-[2-diphenylmethoxy)ethyl]-3-(2-methoxyphenyl) pyrrolidine maleate

Proceeding as in Example 1, using 17.5 g (60 mmole) of 1-(diphenylmethoxy)-2-bromoethane, 10.6 g (60 mmole) of 3-(2-methoxyphenyl)pyrrolidine [J. R. Rice and D. V. Lopiekes, U.S. Pat. No. 2,975,193] and 16.6 g (120 mmole) of potassium carbonate, there was obtained after silica gel column filtration and maleate conversion, 7.1 g (yield: 24%) of the desired product.

F = 97°–99° C. (acetone-ether)

Elemental analysis: $C_{30}H_{33}NO_6$ (M = 503.60)

|  | C % | H % | N % |
|---|---|---|---|
| Calculated | 71.55 | 6.61 | 2.78 |
| Obtained | 71.53 | 6.53 | 2.71 |

EXAMPLE 14

1-[2-bis(4-fluorophenyl)methoxy]-3-(3-isopropoxyphenyl)pyrrolidine fumarate

Proceeding as in Example 9, using 16.4 g (50 mmole) of 1-[bis(4-fluorophenyl)methoxy]-2-bromoethane, 10.3 g (50 mmole) of 3-(3-1isopropoxyphenyl)pyrrolidine and 13.8 g (100 mmole) of potassium carbonate, there was obtained after silica gel column filtration, 16.4 g (yield: 73%) of 1-[2-[bis(4-fluorophenyl) methoxy]ethyl]-3-(3-isopropoxyphenyl)pyrrolidine.

The fumarate was prepared using the traditional method.

F = 121°–124° C. (ethanol-water)

Elemental analysis: $C_{32}H_{35}F_2NO_6$ (M = 567.63)

|  | C % | H % | F % | N % |
|---|---|---|---|---|
| Calculated | 67.71 | 6.22 | 6.69 | 2.47 |
| Obtained | 67.65 | 6.20 | 6.66 | 2.40 |

The (3-(3-isopropoxyphenyl)pyrrolidine was prepared using the method described by A. Ebnother and K. Hasspacher (Swiss Patent No. 526 536) using 3-isopropoxybenzaldehyde.

Boiling point$_{0.5}$ = 110–114° C.

EXAMPLE 15

1-[2-[bis(4-fluorophenyl)methoxy]ethyl]-3-(3,5-dimethoxyphenyl)pyrrolidine fumarate Proceeding as in Example 9, using 14.8 g (45 mmole) of 1-[bis(4-fluorophenyl)methoxy]-2-bromoethane, 9.4 g (45 mmole) of 3-(3,5-dimethoxyphenyl)pyrrolidine and 12 g (86 mmole) of potassium carbonate, there was obtained after silica gel column chromatography (eluent chloroform-methanol, 9/1), 9.5 g (yield: 46%) of 1-[2-[bis(4-fluorophenyl)methoxy]ethyl]-3-(3,5-dimethoxy phenyl)pyrrolidine.

The fumarate was prepared using the traditional method.

F=106°-108° C. (acetone-ether)

Elemental analysis: $C_{31}H_{33}F_2NO_7$ (M=569.60)

|  | C % | H % | F % | N % |
|---|---|---|---|---|
| Calculated | 65.37 | 5.84 | 6.67 | 2.46 |
| Obtained | 65.35 | 5.82 | 6.57 | 2.40 |

The 3-(3,5-dimethoxyphenyl)pyrrolidine was prepared using the A. Ebnother and K. Hasspacher method (Swiss Patent No. 526 536) using 3,5-dimethoxybenzaldehyde.

Boiling point$_{0.4}$=132-138° C.

EXAMPLE 16

1-[2-[bis(4-fluorophenyl)methoxy]ethyl]-2-(3-methoxyphenyl)pyrrolidine fumarate

Proceeding as in Example 9, using 9.8 g (30 mmole) of 1-[bis(4-fluorophenyl)methoxy]-2-bromoethane, 5.3 g (30 mmole) of (2-(3-methoxyphenyl)pyrrolidine and 8.3 g (60 mmole) of potassium carbonate, there was obtained after silica gel column filtration, 6.7 g (yield: 52%) of 1-[2-[bis(4-fluorophenyl)methoxy]ethyl]-2-(3-methoxyphenyl)pyrrolidine.

The fumarate was prepared using the traditional method.

F=134°-136° C. (acetone)

Elemental analysis: $C_{30}H_{31}F_2NO_6$ (M=539.58)

|  | C % | H % | F % | N % |
|---|---|---|---|---|
| Calculated | 66.78 | 5.79 | 7.04 | 2.60 |
| Obtained | 66.49 | 5.88 | 7.03 | 2.45 |

EXAMPLE 17

1-[2-(diphenylmethoxy)ethyl]-3-phenylpiperidine oxalate (a) (Diphenylmethoxy) acetyl chloride 8.1 g (68.1 mmole) of thionyl chloride was added to a solution of 5.5 g (22.7 mmole) of (diphenylmethoxy) acetic acid in 150 cm$^3$ of benzene. The solution was refluxed for 5 hours, then evaporated to dryness under reduced pressure. Distillation of the residue yielded 4.3 g (yield: 73%) of (diphenylmethoxy) acetyl chloride.

Boiling Point$_{0.25}$=115°-125° C.

(b) 1-[diphenylmethoxy)acetyl]-3-phenylpiperidine

A solution of 4.5 g (17.2 mmole) of (diphenylmethoxy) acetyl chloride in 50 cm$^3$ of methylene chloride was added drop-wise at room temperature to a solution of 2.8 g (17.2 mmole) of 3-phenylpiperidine [prepared according to M. Julia et al., Bull. Soc. Chim. Fr. 1968, 987] and 3.5 g (34.4 mmole) of triethylamine in 100 cm$^3$ of methylene chloride. The reaction mixture was heated to reflux for 4 hours; it was allowed to stand overnight and was then poured into a solution of 10 cm$^3$ of concentrated hydrochloric acid in 300 cm$^3$ of water. The mixture was extracted with methylene chloride, washed with water and dried on sodium sulfate. After the solvent was evaporated under reduced pressure, the residue was purified by silica gel filtration (eluent, hexaneethyl acetate, 1/1), then by recrystallization from a hexane-ethyl acetate mixture. There was obtained 4.3 g (yield: 65%) of 1-[(diphenylmethoxy)acetyl]-3-phenylpiperidine.

F=102°-103° C.

Elemental analysis:

|  | C % | H % | N % |
|---|---|---|---|
| Calculated | 81.01 | 7.06 | 3.63 |
| Obtained | 81.04 | 7.16 | 3.49 |

(c) 1-[2-(diphenylmethoxy)ethyl]-3-phenylpiperidine oxalate

A solution of 3 g (7.78 mmole) of 1-[(phenylmethoxy)acetyl]-3-phenylpiperidine in 30 cm$^3$ of tetrahydrofuran was added dropwise to a solution of 0.5 g (12.4 mmole) of lithium aluminum hydride in 50 cm$^3$ of tetrahydrofuran. The mixture was heated to reflux for 4 hours, left overnight, and then hydrolyzed by the addition of 2.5 cm$^3$ of water. It was diluted with 100 cm$^3$ of ether. The alkaline sediments are separated and washed with ether. The ethereal phases were collected, dried on sodium sulfate and concentrated under reduced pressure. The residue was dissolved in 20 cm$^3$ of acetone. A solution of 0.75 g (8.3 mmole) of oxalic acid in 30 cm$^3$ of acetone was added. The oxalate precipitate was filtered, and recrystallized from acetone.

Yield: 1.6 g (44.5%)

F=90°-92° C.

Elemental analysis: $C_{28}H_{31}NO_5$ (M=461.56)

|  | C % | H % | N % |
|---|---|---|---|
| Calculated | 72.86 | 6.77 | 3.03 |
| Obtained | 73.09 | 6.90 | 3.15 |

NMR DMSO d$_6$+CF$_3$COOD)δ=1.4-2.1 (multiplet, 4H); 2.5-4.0 (multiplet, 9H); 5.4 (singlet, 1 H); 7.2 (singlet, 15H).

EXAMPLE 18

1-[2-(diphenylmethoxy)ethyl]-4-phenylpiperidine oxalate.

(a) 1-[(diphenylmethoxy)acetyl]-4-phenylpiperidine

Proceeding as in Example 17, using 4.5 g (17.2 mmole) of (diphenylmethoxy) acetyl chloride and 2.8 g (17.2 mmole) of phenyl-4 piperidine, there was obtained after silica gel filtration (eluent hexane-ethyl acetate, 1/1) and recrystallization from a hexane-ethyl acetate mixture, 4.8 g (yield: 72%) of 1-[(diphenylmethoxy)acetyl]-4-phenylpiperidine.

F=96°-98° C.

Elemental analysis: $C_{26}H_{27}NO_2$

| | C % | H % | N % |
|---|---|---|---|
| Calculated | 81.01 | 7.06 | 3.63 |
| Obtained | 80.81 | 7.06 | 3.60 |

(b) 1-[2-(diphenylmethoxy)ethyl]-4-phenylpiperidine oxalate

A solution of 7.4 g (18.6 mmole) of 1-[(diphenylmethoxy) acetyl]-4-phenylpiperidine in 60 cm³ of tetrahydrofuran was added to a solution of 1.1 g (29.7 mmole) of lithium aluminum hydride in 100 cm³ of tetrahydrofuran. The mixture was heated to a reflux for 12 hours and, after cooling to room temperature, hydrolyzed with 5.5 cm³ of water. 200 cm³ of ether was added. The alkaline residues were washed with ether. The ethereal solutions were collected, dried on sodium sulfate and concentrated under reduced pressure. The residue was dissolved in 30 cm³ of acetone. A solution of 1.7 g (18.9 mmole) of oxalic acid in 150 cm³ of acetone was added. The 1-[2-(diphenylmethoxy)ethyl]-4-phenyl piperidine oxalate precipitate was filtered, then recrystallized from an acetone-ethanol mixture.

Yield: 5.1 g (59%)
F=163°-164° C.
Elemental analysis: $C_{28}H_{31}NO_5$ (M=461.56)

| | C % | H % | N % |
|---|---|---|---|
| Calculated | 72.86 | 6.77 | 3.03 |
| Obtained | 72.70 | 6.78 | 3.09 |

EXAMPLE 19

1-[2-(diphenylmethoxy)ethyl]-3-(3-methoxyphenyl) piperidine oxalate

(a)

1-[2-(diphenylmethoxy)acetyl]-3-(methoxyphenyl)-piperidine.

A solution of 2.8 g (10.9 mmole) of (diphenylmethoxy) acetyl chloride in 25 cm³ of methylene chloride was added quickly to a solution of 2.1 g (10.9 mmole) of (3-(3-methoxyphenyl) piperidine [prepared using the B. M. Iselin and K. Hoffmann method, Helv. Chim. Acta 1954, 37, 178] and 2.2 g (21.8 mmole) of triethylamine in 75 cm³ of methylene chloride. The solution was brought to reflux and maintained at reflux for 10 hours, then poured into a solution of 10cm³ of hydrochloric acid in 300 cm³ of water. The mixture was extracted with methylene chloride, washed with water and dried on sodium sulfate. After the solvent was evaporated under reduced pressure, the residue was purified using silica gel chromatography (eluent,hexane-ethyl acetate, 1/1). There was obtained 3.3 g (yield: 73%) of 1-[(diphenylmethoxy)acetyl]-3-(methoxyphenyl)piperidine.

Elemental analysis:

| | C % | H % | N % |
|---|---|---|---|
| Calculated | 78.04 | 7.03 | 3.37 |
| Obtained | 77.79 | 6.75 | 3.41 |

(b) 1-[2-(diphenylmethoxy)ethyl]-3-(3-methoxyphenyl)-piperidine oxalate

A solution of 6.6 g (15.9 mmole) of 1-[(diphenylmethoxy)acetyl]-3-(methoxyphenyl)piperidine in 50 cm³ of tetrahydrofuran was added dropwise to a solution of 0.96 g (25.4 mmole) of lithium aluminum hydride in 100 cm³ of tetrahydrofuran. The mixture was brought to reflux for 5 hours, allowed to stand overnight, then hydrolyzed by the addition of 5 cm³ of water. The alkaline residues were separated. The solution was concentrated under reduced pressure. The residue was treated with a solution of 1.5 g (16.7 mmole) of oxalic acid in 100 cm³ of acetone. The 1-[2-(diphenylmethoxy)ethyl]-3-(3-methoxyphenyl)piperidine oxalate precipitate was filtered and recrystallized from acetone.

Yield: 3.0 g (38%)
F=80°-86° C.
Elemental analysis: $C_{29}H_{33}NO_6$ (M=491,58)

| | C % | H % | N % |
|---|---|---|---|
| Calculated | 70.86 | 6.77 | 2.85 |
| Obtained | 70.79 | 6.62 | 2.89 |

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

What is claimed is:

1. 1-[(diarylmethoxy)alkyl]pyrrolidines and piperidines having the following formula:

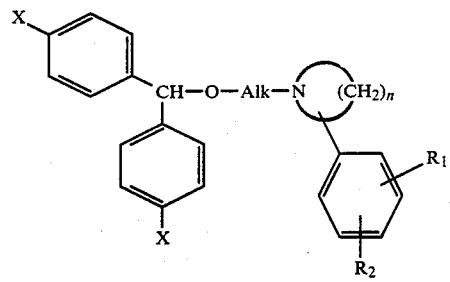

wherein X is selected from the group consisting of hydrogen and fluorine; Alk is selected from the group consisting of linear-chain and branched alkyl groups containing two or three carbon atoms; $R_1$ and $R_2$ are selected from the group consisting of hydrogen and linear-chain or branched alkoxy radicals having from 1 to 4 carbon atoms; n is 4 or 5; and their pharmaceutically-acceptable mineral and organic acid salts.

2. 1-[(diarylmethoxy)alkyl]pyrrolidines and piperidines according to claim 1, wherein Alk is a linear-chain radical containing two or three carbon atoms; and their pharmaceutically-acceptable mineral and organic acid salts.

3. 1-[(diarylmethoxy)alkyl]pyrrolidines and piperidines according to claim 1, wherein Alk is the ethylene radical —CH₂—CH₂—; and their pharmaceutically-acceptable mineral and organic acid salts.

4. 1-[(diarylmethoxy)alkyl]pyrrolidines and piperidines according to claim 1, wherein Alk is the ethylene radical —CH₂—CH₂— and n is 4; and their pharmaceutically-acceptable mineral and organic acid salts.

5. The compound 1-[2-(diphenylmethoxy)-ethyl]-3-(3-methoxyphenyl)pyrrolidine and its pharmaceutically-acceptable mineral and organic acid salts.

6. The compound 1-[2-[bis(4-fluorophenyl)methoxy]ethyl]-3(3-methoxyphenyl)pyrrolidine and its pharmaceutically- acceptable mineral and organic acid salts.

7. A pharmaceutical composition comprising an effective amount of a 1-[(diarylmethoxy)alkyl]pyrrolidine or piperidine having the following formula as a main active ingredient:

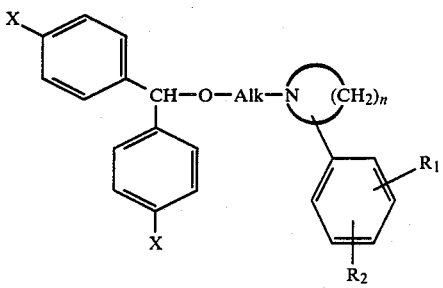

wherein X is selected from the group consisting of hydrogen and fluorine atom; Alk is selected from the group consisting of linear-chain and branched alkyl groups containing two or three carbon atoms; $R_1$ and $R_2$ are selected from the group consisting of hydrogen and linear-chain and branched alkoxy radicals having from 1 to 4 carbon atoms; n is 4 or 5; and their pharmaceutically-acceptable mineral acid or organic salts.

* * * * *